United States Patent
Fukutani et al.

(10) Patent No.: US 7,829,362 B2
(45) Date of Patent: Nov. 9, 2010

(54) FIELD-EFFECT TRANSISTOR, SENSOR USING IT, AND PRODUCTION METHOD THEREOF

(75) Inventors: Kazuhiko Fukutani, Santa Cruz, CA (US); Takao Yonehara, Atsugi (JP); Hirokatsu Miyata, Hadano (JP); Yohei Ishida, Kawasaki (JP); Tohru Den, Setagaya-ku (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/945,838

(22) Filed: Nov. 27, 2007

(65) Prior Publication Data

US 2008/0076201 A1 Mar. 27, 2008

Related U.S. Application Data

(62) Division of application No. 10/530,549, filed as application No. PCT/JP2004/011529 on Aug. 4, 2004, now Pat. No. 7,329,387.

(30) Foreign Application Priority Data

Aug. 11, 2003 (JP) .............................. 2003-291523

(51) Int. Cl.
    *H01L 21/336* (2006.01)
(52) U.S. Cl. ................... 438/49; 438/960; 257/E21.409
(58) Field of Classification Search ................. 438/409, 438/911, 960, 48–49, 784; 257/253, E21.409
    See application file for complete search history.

(56) References Cited

U.S. PATENT DOCUMENTS

| 4,320,168 | A | * | 3/1982 | Lindmayer | 428/332 |
| 5,201,681 | A | | 4/1993 | Okunuki et al. | 445/24 |
| 5,306,661 | A | * | 4/1994 | Tonucci et al. | 438/494 |
| 5,359,214 | A | * | 10/1994 | Kurtz et al. | 257/287 |
| 5,361,015 | A | | 11/1994 | Okunuki et al. | 313/309 |
| 5,362,972 | A | * | 11/1994 | Yazawa et al. | 257/13 |

(Continued)

FOREIGN PATENT DOCUMENTS

JP 56-76043 6/1981

(Continued)

OTHER PUBLICATIONS

A. Huczko, "Template-Based Synthesis of Nanomaterials", Mar. 8, 2000, p. 365-376, Applied Physics A Materials Science & Processing.

*Primary Examiner*—Matthew W Such
(74) *Attorney, Agent, or Firm*—Fitzpatrick, Cella, Harper & Scinto

(57) ABSTRACT

A sensor which has high measuring sensitivity and is excellent in response is provided by forming a porous film in a sensitive section of a field-effect transistor. It comprises a porous body, which is formed on a sensitive section (here, a gate insulating film) of the field-effect transistor and has cylindrical pores which are formed almost perpendicularly to a substrate, and the field-effect transistor. It uses as a porous film a porous film which is made of a semiconductor material whose main component (except oxygen) is silicon, germanium, or a composite of silicon and germanium, or a porous film made of an insulation material whose main component is silicon oxide, which has pores perpendicular to the substrate.

1 Claim, 8 Drawing Sheets

U.S. PATENT DOCUMENTS

| | | | |
|---|---|---|---|
| 5,422,302 A | 6/1995 | Yonehara et al. | 437/83 |
| 5,458,755 A | 10/1995 | Fujiyama et al. | 204/224 |
| 5,726,464 A | 3/1998 | Kumomi et al. | 257/103 |
| 5,874,047 A | 2/1999 | Schöning et al. | 422/82.02 |
| 5,899,734 A * | 5/1999 | Lee | 438/584 |
| 6,027,796 A * | 2/2000 | Kondoh et al. | 428/312.8 |
| 6,278,231 B1 | 8/2001 | Iwasaki et al. | 313/310 |
| 6,309,945 B1 | 10/2001 | Sato et al. | 438/409 |
| 6,448,155 B1 | 9/2002 | Iwasaki et al. | 438/464 |
| 6,468,663 B1 | 10/2002 | Sato et al. | 428/446 |
| 6,468,923 B1 | 10/2002 | Yonehara et al. | 438/761 |
| 6,479,365 B2 * | 11/2002 | Lee et al. | 438/409 |
| 6,613,676 B1 | 9/2003 | Yonehara et al. | 438/691 |
| 6,936,854 B2 | 8/2005 | Iwasaki et al. | 257/81 |
| 6,972,146 B2 | 12/2005 | Den et al. | 428/138 |
| 2002/0034646 A1 | 3/2002 | Canham | 428/446 |
| 2003/0020060 A1 | 1/2003 | Iwasaki et al. | 257/13 |
| 2003/0153151 A1* | 8/2003 | Choi et al. | 438/257 |
| 2004/0043208 A1 | 3/2004 | Fukutani et al. | 428/304.4 |
| 2005/0053773 A1 | 3/2005 | Fukutani et al. | 428/209 |
| 2005/0062033 A1 | 3/2005 | Ichihara et al. | 257/17 |
| 2006/0021564 A1* | 2/2006 | Norman et al. | 117/84 |
| 2006/0043410 A1 | 3/2006 | Iwasaki et al. | 257/103 |
| 2006/0060924 A1 | 3/2006 | Ogawa et al. | 257/364 |

FOREIGN PATENT DOCUMENTS

| | | |
|---|---|---|
| JP | 61-218932 A | 9/1986 |
| JP | 63090754 | 4/1988 |
| JP | 10-504388 A | 4/1998 |
| JP | 10-185864 | 7/1998 |
| JP | 2000-031462 A | 1/2000 |
| WO | WO 03/069677 | 8/2003 |
| WO | WO 2004039731 A2 * | 5/2004 |

* cited by examiner

FIELD-EFFECT TRANSISTOR, SENSOR USING IT, AND PRODUCTION METHOD THEREOF

RELATED APPLICATIONS

This application is a division of U.S. application Ser. No. 10/530,549, filed Jan. 30, 2006, which was filed under 35 U.S.C. §371 based on the application PCT/JP04/11529, filed Aug. 4, 2004, the entire disclosure of which is incorporated herein.

TECHNICAL FIELD

The present invention relates to a field-effect transistor using a porous film which has pores with a cylindrical shape vertical to a substrate on a sensitive section (gate insulating film etc.) of the field-effect transistor, and a sensor using it, and in particular, relates to a sensor, which transduces a chemical or physical change into an electric change, such as a gas sensor detecting a gas (gas molecules etc.), a biosensor detecting a biomaterial such as protein, or a pH sensor detecting pH in a solution.

BACKGROUND ART

Up to now, sensors using a field-effect transistor have been known widely (Japanese Patent Application Laid-Open No. S56-76043). Among them, plenty of attempts to enhance measuring sensitivity to a detection object material by forming a nano structure on a sensitive section of a field-effect transistor have been done. For example, a sensor is disclosed, the sensor in which a nano structure (a structure constituted by a plurality of material particles (clusters)) was formed in a sensitive section of a field-effect transistor, so as to raise the mechanical fixation of biogenic substances (a cell, a receptor, gamma-globulin, etc.) to a sensor sensitive section, and further, to enhance a signal transmission characteristic and measuring sensitivity (Japanese Patent Application Laid-Open No. H10-185864). Specifically, this is structured so that an active contact surface of the sensor may mostly coincide with a contour shape of the outside of each biogenic substance.

DISCLOSURE OF THE INVENTION

Nevertheless, in a conventional method, as shown in FIG. 9, since the structure in a nano meter level is formed by material particles (clusters) being implanted into the sensitive section of the sensor, it is very hard to control the shape of the structure so as to mostly coincide with the contour shape of the outside of the biogenic substance. In addition, although it is shown that it is possible to produce a porous layer, it is very hard to control the diameter of its pores, its pore density, etc., and it is very difficult to make biomolecules carried into the pores in high density. Furthermore, depending on a formation method, there is a possibility of making a defect and the like arise in the sensor sensitive sections (gate insulating film etc.) and reducing the measuring sensitivity. In FIG. 9, reference numeral 9 denotes a field-effect transistor, reference numeral 12 denotes a silicon oxide layer, reference numeral 15 denotes a contact surface coating, reference numeral 16 denotes a cluster, reference numeral 17 denotes a gap, reference numeral 18 denotes an immune receptor, reference numeral 19 denotes a holding area, reference numeral 20 denotes a tip end, and reference numeral 24 denotes an active contact surface.

Then, the present invention provides a field-effect transistor, and a sensor using it, the field-effect transistor which has high measuring sensitivity and is excelled in response by forming a porous film in the sensitive section of the field-effect transistor, the porous film which has cylindrical pores which are perpendicular to a substrate, and have high pore density and 20 nm or less of pore diameter.

Furthermore, the present invention provides a production method for simply producing the above-mentioned sensor, using the field-effect transistor, in low cost.

In order to solve the above-mentioned problems, the present invention, a first invention of this application is a sensor which reads electrically a physical or chemical change of a sensitive section by gas molecules, biomolecules, or the like with a field-effect transistor, and is characterized in having a porous film which has cylindrical pores, which are perpendicular to a substrate, in the sensitive section of the field-effect transistor. In addition, the sensor of the present invention is characterized in that a material which constitutes the porous film is made of a semiconductor material or an insulation material.

In particular, when the material which constitutes the porous film is the semiconductor material, it is desirable that it is a material using silicon, germanium, or a composite of silicon and germanium as a main component. Furthermore, it is more preferable that the semiconductor material is in crystallinity than in an amorphous state.

In addition, in particular, when the material which constitutes the porous film is the insulation material, it is desirable that it is a silicon oxide.

Furthermore, as for the pores in the porous film, it is preferable that an average pore size is 20 nm or less, and mean density is $1.5 \times 10^{11}$ pores/cm$^2$ or larger. Thereby, since surface areas of the pores in the porous film become remarkably large, bonding sites of the detection material increase and measuring sensitivity increases remarkably. In particular, since the detection material can adhere to the entire pore surfaces of the pores in the porous film when being small molecules such as gas molecules like a gas, it is possible to remarkably increase the sensitivity.

In addition, the sensor of the present invention is characterized in making the sensitive section of the field-effect transistor cause an electric potential change by a selective reaction between a detected material adhering to the porous film surface, and the detection material when the detection material is biological material. Thereby, since the detection material stably binds together in the porous film, stable measurement becomes possible. Moreover, since biomolecules can be held more stably than the usual by introducing them inside the pores, it is possible to hold them operably for a long time.

Furthermore, a second invention of this application is a production method of a sensor characterized in having a step of preparing on a sensitive section of a field-effect transistor a structure that a pillar-shaped material constituted with including a first component disperses in a member constituted with including a second component which is a semiconductor material which can form a eutectic with the first component, a step of removing the pillar-shaped material to form a porous film, and a step of annealing the porous film which has pillar-shaped holes obtained by the removing step.

Moreover, in the second invention, it is desirable that the pillar-shaped material is aluminum and the member is silicon, germanium, or silicon germanium.

Since it is possible to form pores only at the film forming step and removal step when the porous film to which detection object materials such as gas molecules and biomolecules are made to adhere is formed by such a method, it is not necessary to use semiconductor processes such as photolithography for pore formation, and hence, it is possible to produce the sensor in low cost.

With explaining the process of arriving at accomplishing the present invention, the present inventor and et al. obtained the following knowledge when having carried our investigation, regarding a microstructure using aluminum, forward.

Namely, we found out that there was the case that aluminum with pillar-shaped structure was formed in silicon, germanium, or a complex of silicon and germanium in self-formation under predetermined conditions when adding semiconductor materials such as silicon and germanium at the time of forming an aluminum film on a substrate by a deposition method, which forms a material in a non-equilibrium state, such as a sputtering method. In addition, it turned out that a porous film, made of a semiconductor material (oxygen may be included) with pore diameter and pore density, which are hard to be formed by conventional methods, could be formed by dipping a film, on which aluminum with the pillar-shaped structure was formed, in the solution which dissolved aluminum preferentially to silicon, germanium, or a complex of silicon and germanium. Furthermore, the porous film formed here is an amorphous material. Moreover, when the porous film made of the semiconductor material in an amorphous state was crystallized by thermal annealing, this porous film became to show a semiconductor characteristic showing p-type conduction. In addition, it turned out that, when detection object materials such as gas molecules were made to adhere to a surface of the porous film, the electric conductivity (for example, electronic conduction state) of the porous film changes largely. Furthermore, when the porous film was formed on the sensitive section of the field-effect transistor, the detection object material was detectable in further high sensitivity.

Then, the present inventors advanced the investigation wholeheartedly on the basis of the above-mentioned knowledge, and became to accomplish the present invention.

In addition, in the porous film which is formed by removing the pillar-shaped material from the structure that the pillar-shaped material constituted with including the first component in this way dispersed in the member constituted with including the second component which was the semiconductor material which can form a eutectic with the first component, it is possible to form a porous film made of a semiconductor material which has pore diameter and pore density which are hard to attain by prior art. Therefore, since a surface area to which a detection object material is made to adhere becomes remarkably large, it becomes possible to raise the sensitivity of the sensor. Furthermore, since pores have a pillar-like shape almost perpendicular to a film surface and the pore diameter is almost constant to the film surface, adhesion and detachment of the detection object material becomes quick, and hence, it becomes possible to raise the response of the sensor.

According to the present invention, it is possible to provide a sensor, which has higher structural stability, higher sensitivity, and further a higher reaction rate than conventional sensors, by making a porous film, which is formed by removing a pillar-shaped material from a structure where a pillar-shaped material constituted with including a first component disperses in a member constituted with including a second component which can form a eutectic with the first component, an adhesion section to which chemical species such as biomolecules and gas molecules are made to adhere, and forming the porous film on a sensitive section of a field-effect transistor.

In addition, the present invention can provide a production method which can simply produce the above-mentioned sensor in low cost.

BEST MODE FOR CARRYING OUT THE INVENTION

Hereafter, best modes of the present invention will be described with referring to drawings.

Structure of Sensor

Figure 1:
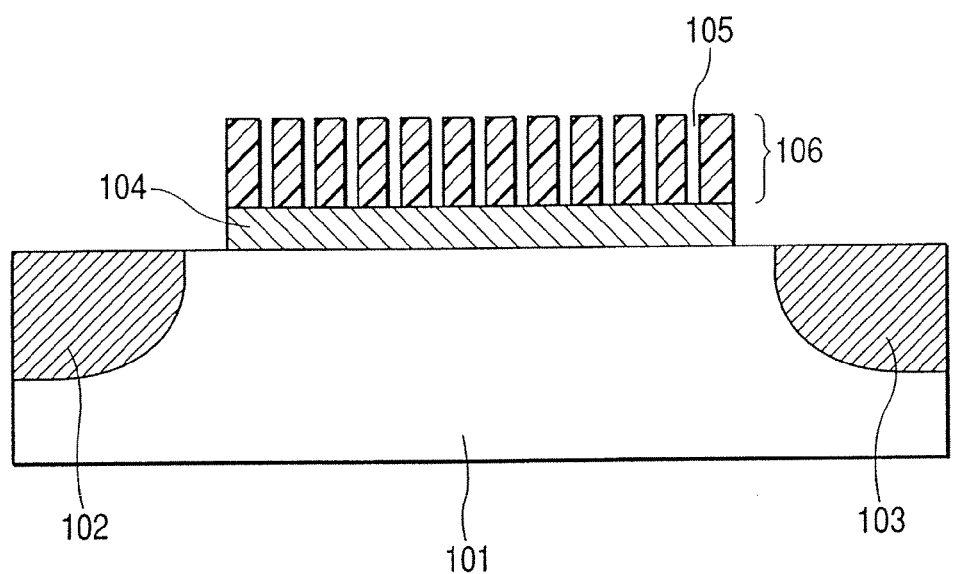
FIG. 1 is a schematic diagram showing an example of a sensor of the present invention.

FIG. 1 is a schematic diagram showing an example of a sensor of the present invention. This example shows an example in which a porous film is formed on a gate insulating film which is a sensitive section of a field-effect transistor, the porous film which has pores which are perpendicular to a substrate and are formed in high density ($1.5 \times 10^{11}$ pores/cm$^2$ or more) in the size of several nm to tens of nm.

In FIG. 1, reference numeral 101 denotes a semiconductor substrate, 102 denotes a source region, 103 denotes a drain region, 104 denotes a gate insulating film which is a sensitive section, 105 denotes a pore, and 106 denotes a porous film. A sensor of the present invention mainly comprises a porous body 106, which is formed on a sensitive section (here, a gate insulating film) of a field-effect transistor and has the cylindrical pores 105 which are formed almost perpendicularly to a substrate, and the field-effect transistor.

Figure 2A:
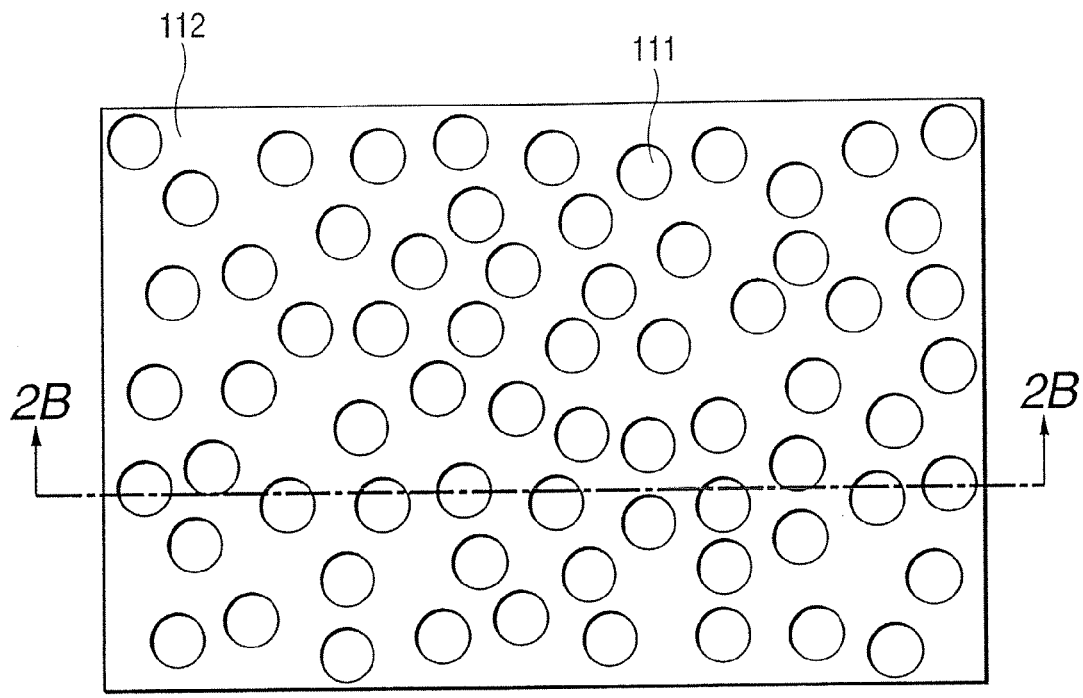
FIGS. 2A and 2B are schematic diagrams showing an example of a porous body used in the sensor of the present invention.
Figure 2B:
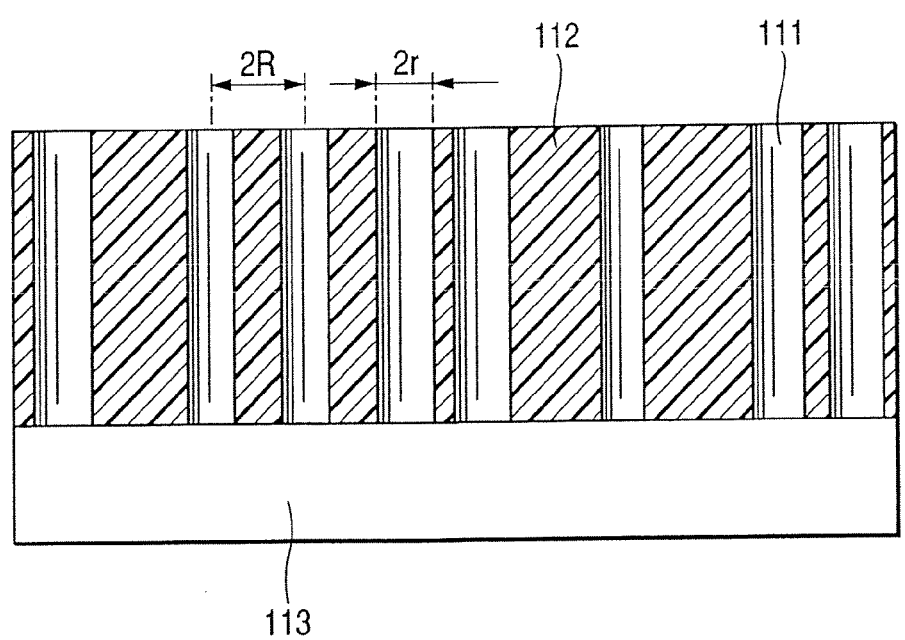

FIGS. 2A and 2B show an example of the porous film used in the sensor of the present invention. FIG. 2A is a schematic diagram in view of a film surface, and FIG. 2B shows a schematic diagram of a cross section taken in 2B-2B of the porous body in FIG. 2A. Reference numeral 111 denotes a pore, 112 denotes a member constituting the porous film, and 113 denotes the sensitive section (here, the gate insulating film) of the field-effect transistor.

The sensor of the present invention is characterized in using as a porous film a porous film, which has pores perpendicular to a substrate, and is made of a semiconductor material whose main component (except oxygen) is silicon, germanium, or a composite of silicon and germanium, or a porous film made of an insulation material whose main component is a silicon oxide. In addition, the pores 111 are separated from each other by the member 112 which comprises the porous film as shown in FIGS. 2A and 2B, and formed perpendicularly or almost perpendicularly to the substrate.

In addition, the pores in the porous film which constitutes the sensor of the present invention have a cylindrical shape as shown in FIG. 2B. Furthermore, the average pore size (this shows the average diameter of the pores in view of the film surface) of pores is not less than 1 nm and not more than 50 nm, and desirably, not less than 1 nm and not more than 20 nm. Moreover, the mean density of pores is at least $1.5 \times 10^{11}$ pores/cm$^2$. The pore diameter shown here denotes $2r$ in FIG. 2B, and a gap between pores denotes $2R$ in FIG. 2B.

Moreover, when the porous film which constitutes the sensor of the present invention is made of a semiconductor material, it is mainly composed of oxygen (because the pore surface is oxidized) and silicon, germanium, or a composite of silicon and germanium, and, in regard to its composition, it is desirable that aluminum is included at not less than 0.1 atomic % and not more than 30 atomic % to all the elements except oxygen, and silicon, germanium, or the composite of silicon and germanium is at not less than 70 atomic % and not more than 99.9 atomic %.

In addition, when the porous film which constitutes the sensor of the present invention made of an insulation material, it is mainly composed of a silicon oxide, and in regard to its composition, it is desirable that aluminum is included at not less than 0.1 atomic % and not more than 30 atomic % to all the elements except oxygen, and silicon is at not less than 70 atomic % and not more than 99.9 atomic %.

Furthermore, although it is desirable that a main component of a structural material of the porous film which constitutes the sensor of the present invention is silicon, germanium, or the composite of silicon and germanium except oxygen, it may contain various kinds of elements such as argon (Ar), nitrogen (N), and hydrogen (H).

In addition, since a surface of the porous film is oxidized typically, oxygen is included when the composition analysis of the porous film is performed even when the structural material of a porous body is a semiconductor material.

Furthermore, although it is preferable that the field-effect transistor which constitutes the sensor of the present invention is a field-effect transistor using a single crystal silicon substrate, or a thin film type field-effect transistor using polycrystalline silicon, amorphous silicon, or an organic semiconductor on an insulating substrate such as glass, it is also satisfactory that it is a field-effect transistor using any material, such as a compound semiconductor, so long as the sensitivity of the sensor is not affected. In addition, typically, it is desirable that the field-effect transistor comprises a source region 102, a drain region 103, and a gate insulating film 104 as shown in FIG. 1.

Moreover, although the gate insulating film 104 which constitutes the sensor of the present invention is silicon oxide typically, it is possible to use various insulating materials such as a hafnium oxide, a silicon nitride, and an aluminum oxide. In addition, it is satisfactory to use any kind of insulating film as the material which constitutes the gate insulating film so long as there is no trouble in the operation of the sensor.

Furthermore, although the sensitive section of the field-effect transistor of the present invention denotes the gate insulating film fundamentally, it may also include an aluminum oxide, a silicon nitride, etc. formed on the gate insulating film (typically, a silicon oxide). Furthermore, an electrode formed on the gate insulating film such as a silicon oxide may be included as the sensitive section of the field-effect transistor of the present invention.

Figure 3:
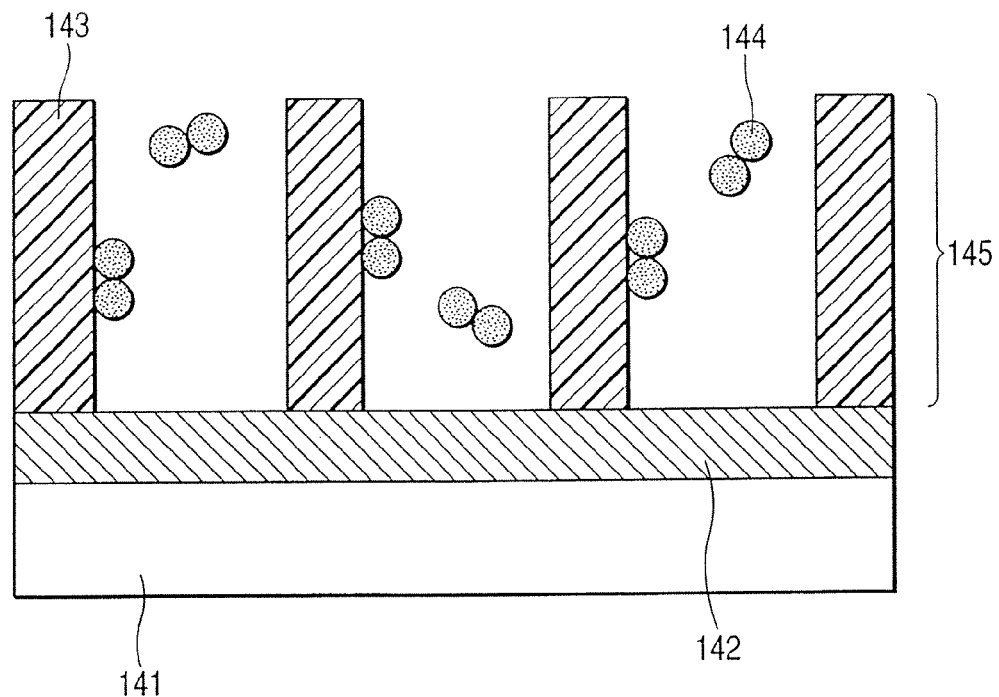
FIG. 3 is a schematic diagram showing an example of a sensor of the present invention.

Moreover, the sensor which has the porous film with such structure changes an electric charge state of the porous film 145 by the adhesion of gas molecules 144 (gas species, etc.) such as $NO_2$, ammonia, moisture molecules, oxygen, and ethanol to the pore surface as shown in FIG. 3. A change of an electrical parameter caused thereby is read by the field-effect transistor, and thereby, it is possible to determine the presence and density of gas molecules. In addition, since the porous film used by the present invention has a remarkably large area which gas molecules adsorbs, a change of the electric charge state is large, and hence, it is possible to perform measurement in higher sensitivity. In FIG. 3, the reference numeral 141 denotes a substrate, the reference numeral 142 denotes a sensitive section (a gate insulating film), and the reference numeral 143 denotes a second component.

Figure 4:
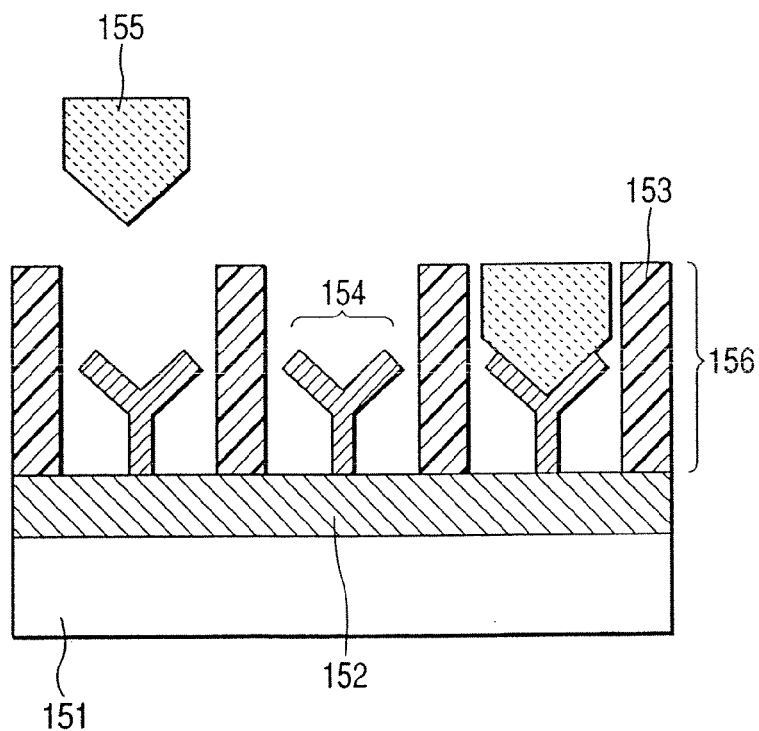
FIG. 4 is a schematic diagram showing an example of a sensor of the present invention.

Furthermore, as shown in FIG. 4, inside the pores in the porous film 156, it is possible to attach a detected material 154 selectively bonded with the detection material 155. In addition, it is possible to modify the surfaces of the pores with a chemical so that only specific detection material may adhere selectively on the pore surfaces in the porous film.

The sensor having the porous film 156 with such structure can fix only the biomolecules, which are the detection material 155, in the pores by introducing the biomolecules, which are the detected material 154 bonded with specific biomolecules, inside the pores as shown in FIG. 4. Since this fixation also changes the electric charge state of the porous film, it is possible to measure the specific presence and an amount of biomolecules by reading an electric change of the field-effect transistor caused by this. In addition, since the biomolecules which are the detected material introduced in the pores are limited on contact with the detected material which is not related to measurement, it is possible to be stably kept for a long time.

In addition, when the biomolecules which are the detected material 154 are introduced in the pores as shown in FIG. 4, the detected material larger than the size of the pores cannot enter into the pores, and hence, it is possible to reduce the decrease of the measuring sensitivity due to the influence of impurity. Furthermore, by optimizing the material quality, pore diameter, and pore density of the porous film which adheres the chemical species such as gas molecules, and biomolecules, it is possible to increase the sensitivity remarkably. In FIG. 4, the reference numeral 151 denotes a substrate, the reference numeral 152 denotes a sensitive section (a gate insulating film), and the reference numeral 153 denotes a second component.

Figure 5:
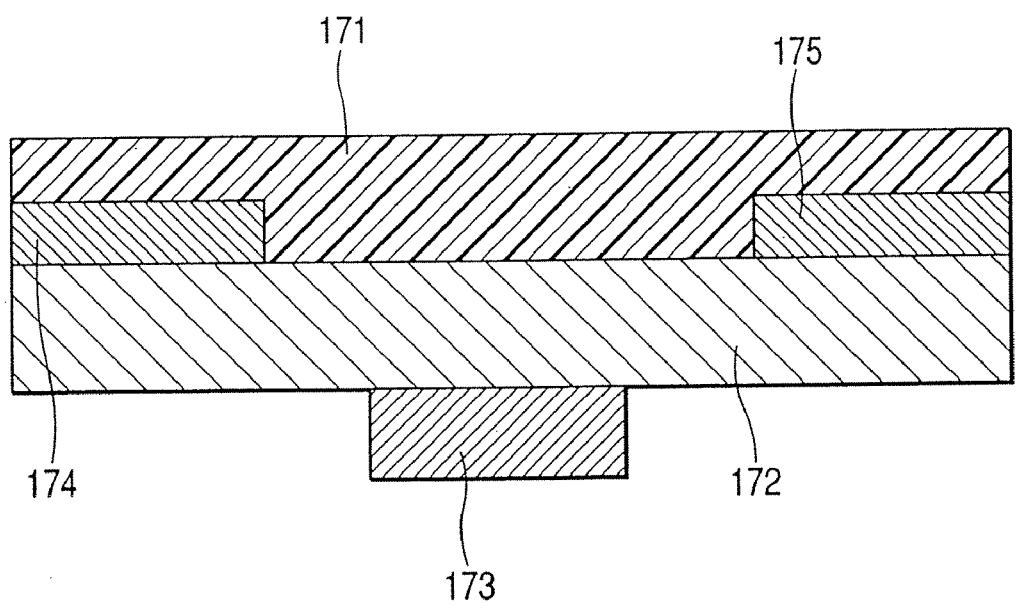
FIG. 5 is a schematic diagram showing an example of a sensor of the present invention.

Furthermore, although the example using the field-effect transistor produced in the substrate was shown in the example of FIG. 1, there is no problem in particular even if thin film type field-effect transistor structure, which is formed on a supporting substrate (not shown) as shown in FIG. 5, is used. In FIG. 5, reference numeral 171 denotes a porous film, 172 denotes a gate insulating film, 173 denotes a gate electrode, 174 denotes a source electrode, and 175 denotes a drain electrode.

Production Method of Sensor

Hereafter, a production method of the sensor by the present invention will be explained in detail. FIGS. 6A, 6B, 6C, 7D, 7E and 7F are explanatory diagrams showing an example of the production method of the sensor of the present invention respectively. It will be explained sequentially in order of 6A to 7F of the Figures. In addition, FIGS. 8A and 8B show an example of the production method of a porous film used in the sensor of the present invention. The feature of this production method is in FIGS. 6B, 6C, and 7D which are a part of forming the porous film to the sensitive section on the field-effect transistor, and it is possible to apply a normal production method of a field-effect transistor to other steps. In addition, although a schematic example of the production method of a field-effect transistor which uses a single crystal substrate is shown here, it is not limited to this.

Figure 6A:
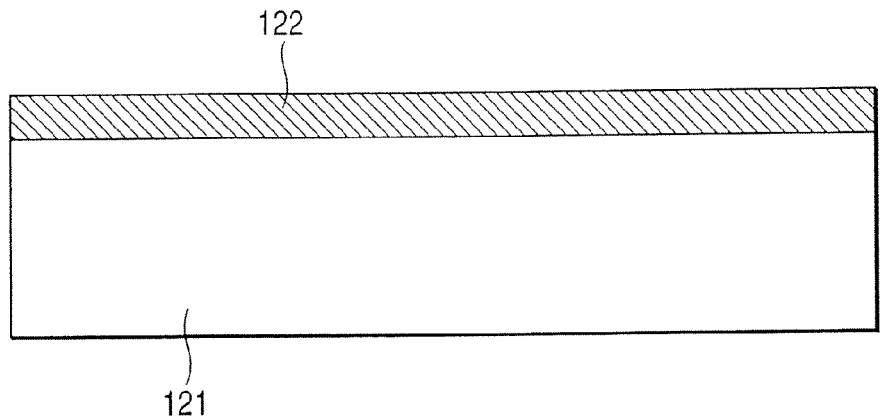
FIGS. 6A, 6B and 6C are explanatory diagrams showing an example of a production method of the sensor of the present invention.

Step in FIG. 6A: A gate insulating film (a sensitive section) 122 is formed. The silicon oxide (the gate insulating film) 122 is formed on a single crystal silicon substrate 121 by using a thermal oxidation method. As a formation method of a gate insulating film, any insulating film forming method such as not only a thermal oxidation method but also a plasma CVD method may be applied.

Figure 6B:
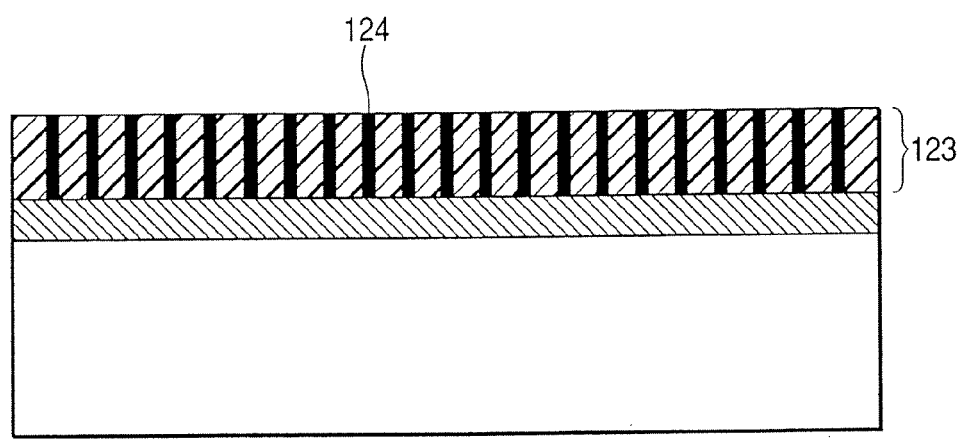

Step in FIG. 6B; Next, a structure (mixed film 123) that a pillar-shaped material constituted with including a first component 124 disperses in a member constituted with including a second component which is a semiconductor material which can form a eutectic with the first component is prepared on the gate insulating film 122.

For example, aluminum and silicon (or, germanium or silicon germanium) which form pillar-shaped structure (the first component) in a matrix (the second component) are prepared, and a structure (an aluminum silicon mixing film, an aluminum germanium mixing film, or aluminum silicon germanium mixing film) is formed on the substrate by a method, which can form a material in a non-equilibrium state, such as a sputtering method.

When the aluminum silicon mixing film, aluminum germanium mixing film, or aluminum silicon germanium mixing film is formed by such a method, aluminum and silicon (or, germanium or silicon germanium) become a micro phase separation film in a metastable state as shown in FIG. 8A, and aluminum forms nano structures (pillar-shaped structures) in several nm level in a silicon (or germanium or silicon germanium) matrix to separate self-organizingly. Aluminum at that time is nearly cylindrical, and its hole size is not less than 1 nm and not more than 50 nm, and preferably, not less than 1 nm and not more than 20 nm. Moreover, the mean density is at least $1.5 \times 10^{11}$ pores/cm$^2$.

In addition, in the mixed film of aluminum and silicon (or, germanium or silicon germanium), an amount of silicon (or, germanium or silicon germanium) in the film formed is 20 to 70 atomic % to a whole amount of aluminum and silicon (or, germanium or silicon germanium), preferably 25 to 65 atomic %, and more preferably 30 to 60 atomic %. Depending also on film formation conditions, when the amount of silicon (or, germanium or silicon germanium) is within this range, it is possible to obtain the aluminum silicon mixing film (or an aluminum germanium mixing film or aluminum silicon germanium mixing film) where aluminum with the pillar-shaped structure disperses in a silicon (or, germanium or silicon germanium) domain.

Atomic % which shows the above-mentioned ratio of aluminum to silicon (or, germanium or silicon germanium) shows a ratio between numbers of atoms of silicon (or, germanium or silicon germanium) and aluminum, it is also described as atom % or at %, and, for example, it is a value when the quantitative analysis of amounts of silicon (or, germanium or silicon germanium) and aluminum in the aluminum silicon mixing film (or, the aluminum germanium mixing film or aluminum silicon germanium mixing film) is performed with inductively coupled plasma emission spectrometry (an ICP method).

Figure 6C:
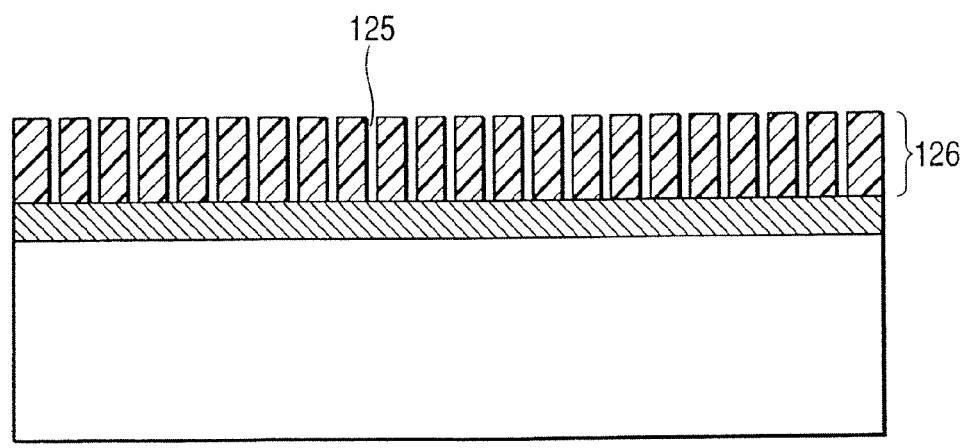

Step in FIG. 6C: Next, the pillar-shaped material is removed. For example, aluminum which is the pillar-shaped material in the above-mentioned aluminum silicon mixing film (or the aluminum germanium mixing film or aluminum silicon germanium mixing film) is etched with a concentrated sulfuric acid, and pores 125 are formed inside the matrix (here, silicon, germanium, or silicon germanium). Thereby, a porous film 126 is obtained, and a porous body as shown in FIG. 8B is formed. In addition, as for the pores in the above-mentioned porous body, pore diameter is not less than 1 nm and not more than 50 nm, and preferably not less than 1 nm and not more then 20 nm, and mean density is at least $1.5 \times 10^{11}$ pores/cm$^2$.

What is preferable as a solution used for the etching is, for example, a concentrated sulfuric acid which dissolves aluminum, hardly dissolves silicon (or germanium), and cannot oxidize silicon easily. Or, when there is no inconvenience in the pore formation by etching, it is possible to use acids such as a phosphoric acid, a sulfuric acid, a hydrochloric acid, and a chromic acid solution, and alkalis such as a sodium hydroxide, and it is limited to neither the type of acids, nor the type of alkalis in particular. In addition, it is satisfactory to use what some types of acid solutions or some types of alkali solutions are mixed. Furthermore, it is possible to suitably set etching conditions such as solution temperature, concentration, and time according to the porous film to be produced.

Figure 7D:
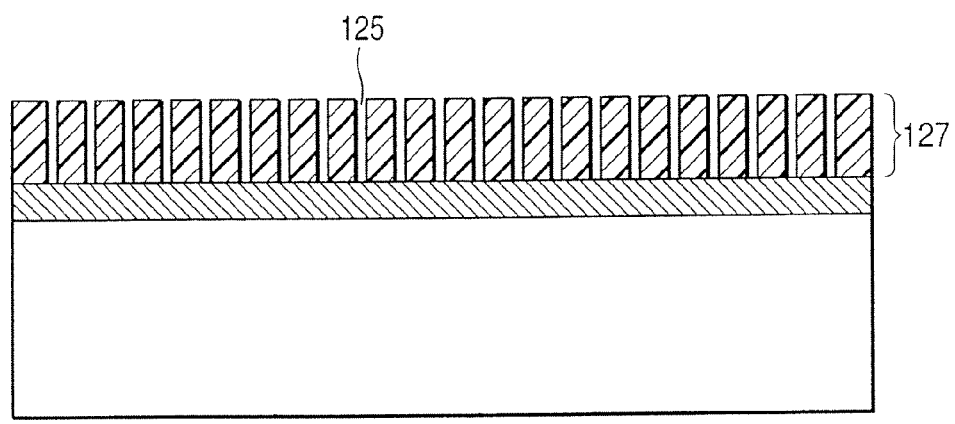
FIGS. 7D, 7E and 7F are explanatory diagrams showing an example of a production method of the sensor of the present invention.
Figure 8A:
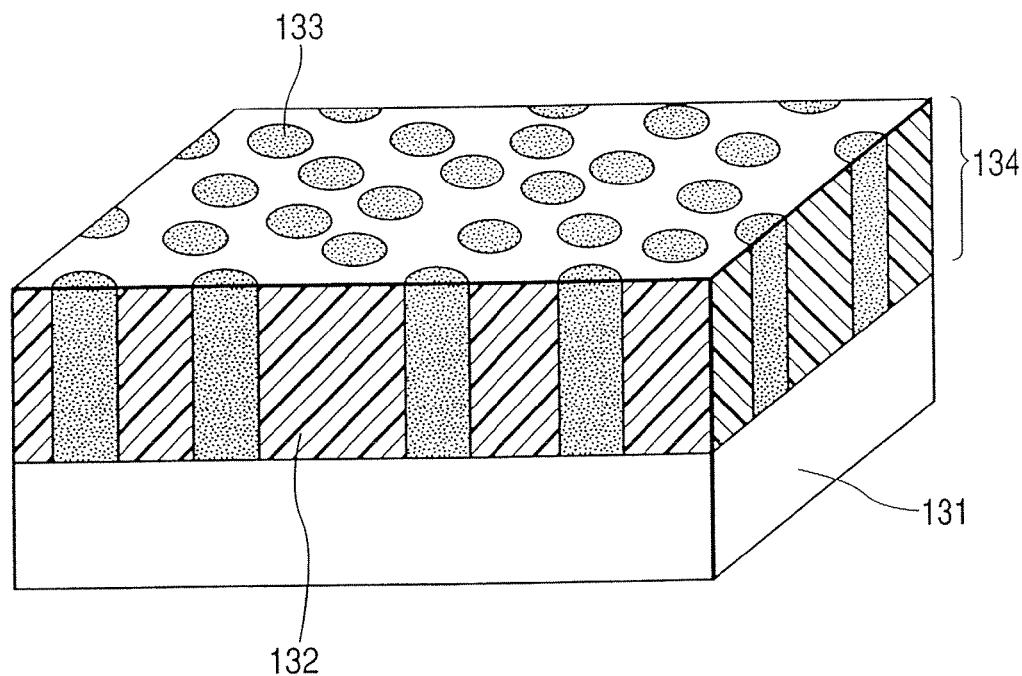
FIGS. 8A and 8B are schematic diagrams showing an example of a production method of a porous film used in the sensor of the present invention.
Figure 8B:
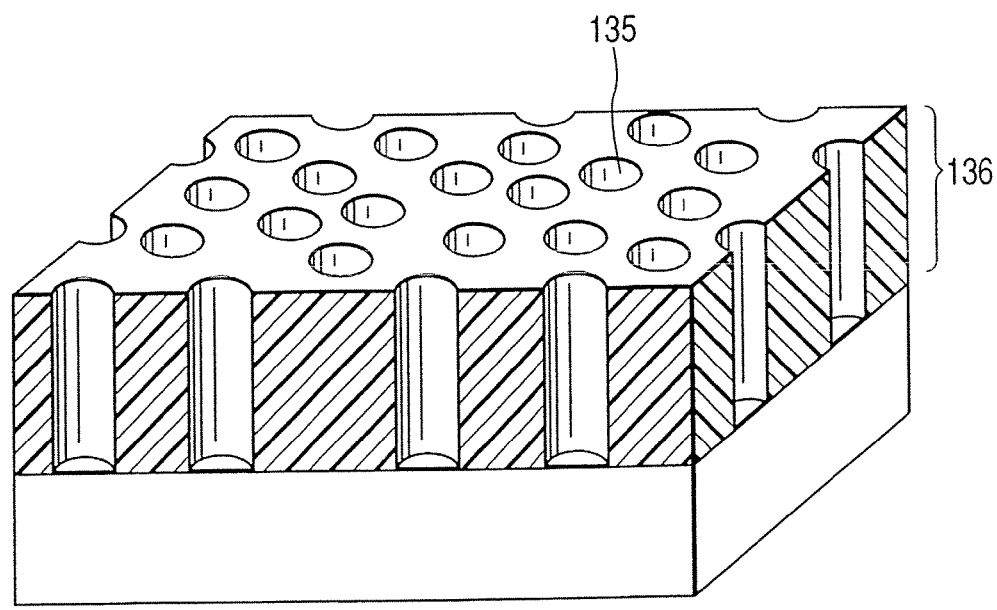
Figure 9:
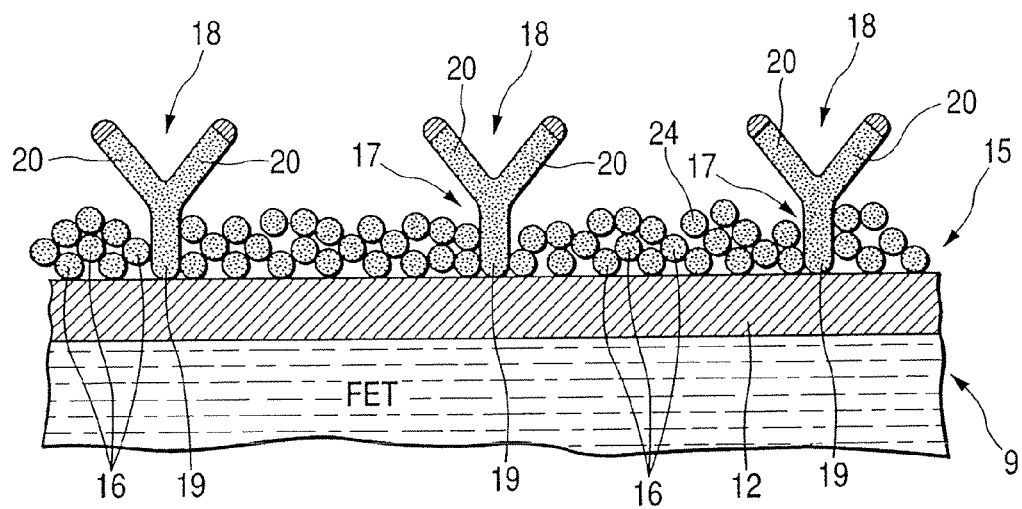
FIG. 9 is an example of a conventional sensor.

Step in FIG. 7D: Next, a single crystal silicon substrate having the porous film 126 which has pillar-shaped holes 125 obtained at the removing step is annealed. Thermal annealing is sufficient as the annealing here, and laser annealing is also sufficient. By performing thermal annealing in an oxygen environment, the porous film 126 is oxidized and becomes an insulating material (a porous film 127). In addition, a porous film 127 made of a semiconductor material having electrical conductivity is formed by performing the thermal annealing and further laser annealing in a reducing atmosphere such as in a hydrogen atmosphere.

Figure 7E:
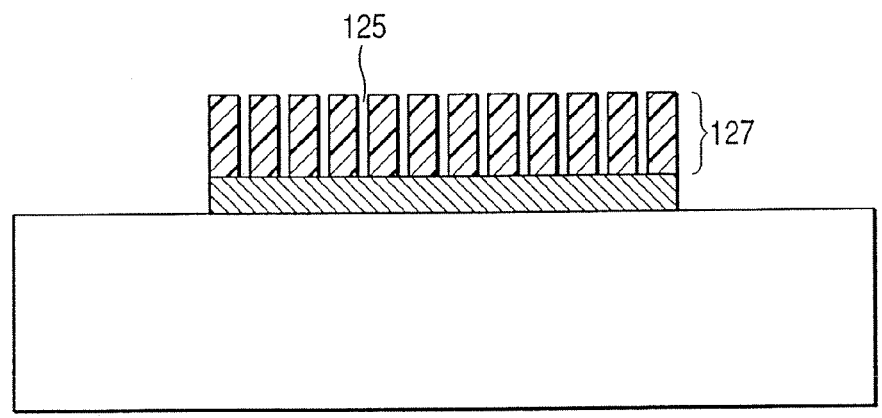

Step in FIG. 7E: Next, the porous film and silicon oxide in an unnecessary portion are removed by photolithography, and dry etching or wet etching.

Figure 7F:
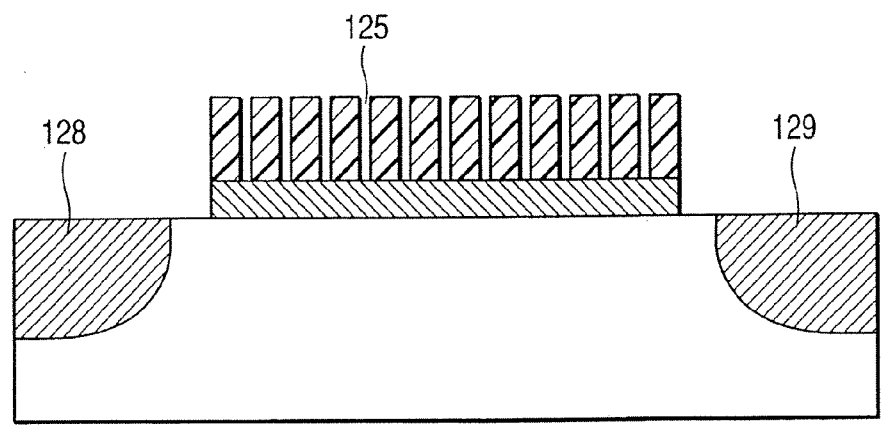

Step in FIG. 7F: Next, a source region 128 and a drain region 129 are formed by using photolithography and an ion implanter.

The sensor which has the porous body film is formed in the sensitive section of the field-effect transistor as shown in FIG. 1 through such a process.

In addition, here, in order to adhere only a specific detection object material to the pore surfaces in the porous film, it is also possible to introduce in the pores the detected material selectively bonded with the detection object material as shown in FIG. 4.

EXAMPLE 1

This example shows the case that a sensor having a porous film, having pores which is perpendicular to a substrate and has a cylindrical shape, on a sensitive section (a gate insulating film) of a field-effect transistor is used as a gas sensor. Here, although the case that a main component except oxygen is silicon as a material which constitutes the porous film is shown, it is possible to adapt almost similar sensor structure, production method, and effects also in the case that a main component except oxygen is germanium or a composite of silicon and germanium.

First, as shown in FIG. 6A, a 50-nm-thick silicon oxide film (a gate oxide film) is formed on a p-type single crystal silicon substrate by the thermal oxidation method. Next, an about 200-nm-thick aluminum silicon mixing film including 50 atomic % of aluminum to the whole amount of aluminum and silicon was formed on the silicon oxide, which is a gate insulating film, by using the magnetron sputtering method as shown in FIG. 6B. A circular aluminum silicon-mixing target with the diameter of 4 inches (101.6 mm) was used as a target. What aluminum powder and silicon powder were sintered at a ratio of 50 atomic %:50 atomic % was used as the aluminum silicon mixing target. Sputter conditions were set at an Ar flow rate of 30 sccm, discharge pressure of 0.15 Pa, and supplied power of 100 W by using RF power. In addition, substrate temperature was set at 100° C.

In addition, the aluminum silicon mixing film was observed with an FE-SEM (field emission scanning electron microscope). In regard to a shape of a surface observed from an obliquely upper direction of the substrate, as shown in FIG. 8A, the circular aluminum pillar-shaped structures (first component (aluminum) 133) surrounded by the silicon domain (second component 132) were arranged two-dimensionally. In FIG. 8A, reference numerical 131 denotes a substrate, reference numerical 134 denotes a mixed film. The average pore diameter of an aluminum pillar-shaped structure portion was 4 nm. In addition, when a cross section was observed with the FE-SEM, each aluminum pillar-shaped structure was mutually independent.

Pores 125 were formed by dipping the aluminum silicon mixing film produced in this way in a 98% of concentrated sulfuric acid solution for 24 hours as shown in FIG. 6C to selectively etch only the aluminum pillar-shaped structure portions. As a result, the porous film 126 which was composed of a member whose main component except oxygen was silicon was produced. In addition, silicon on the surface of the porous film was oxidized.

Next, the aluminum silicon mixing film (porous film which was composed of the member whose main component except oxygen was silicon) having etched with the 98% of concentrated sulfuric acid was observed with the FE-SEM. In regard to a shape of a surface observed from an obliquely upper direction of the substrate, as shown in FIG. 8B, the pores 135 surrounded by the silicon member were arranged two-dimensionally. The hole size of the pores was 4 nm. In addition, the produced porous film 136 was in an amorphous state.

Next, the single crystal silicon substrate on which the porous film produced in this way was formed was annealed at 800° C. in a hydrogen atmosphere. As a result, silicon in the porous film was crystallized and a porous film 127 which is composed of p-type polycrystalline silicon was formed on a silicon oxide (FIG. 7D). Next, the porous film and silicon oxide in unnecessary portions are removed by photolithography, and dry etching or wet etching (FIG. 7E). Furthermore, a source region 128 and a drain region 129 are formed by using photolithography and ion implanter (FIG. 7F). The sensor (gas sensor) which has the porous film composed of polycrystalline silicon as shown in FIG. 7F is formed through such processes.

In addition, when an $NO_2$ amount, an ammonia amount, and a water molecular amount (humidity) were changed in the sensor in which the porous film produced in this way was formed on a sensitive section of a field-effect transistor, the conductance of a channel in the field-effect transistor changed, and the presence and amount of gas molecules were able to be measured.

According to the gas sensor formed in this way, since the pore diameter is 4 nm and pore density is also $1.5 \times 10^{11}$ pores/$cm^2$ or more, it becomes possible to increase a surface area of the porous film remarkably, and hence, to increase measuring sensitivity remarkably. In addition, since it becomes possible to perform quick adhesion and detachment of gas molecules (gas) to/from pore surfaces because pores are almost perpendicular to the substrate and the pore diameter is almost constant, it becomes possible to produce the sensor which is excellent in the response.

EXAMPLE 2

This example shows the case that a sensor having a porous film, having pores which are perpendicular to the substrate and has cylindrical shapes, on a sensitive section (a gate insulating film) of a field-effect transistor is used as a biosensor. Here, the case that a main component which constitutes the porous film is a silicon oxide will be shown.

First, as shown in FIG. 6A, a 50-nm-thick silicon oxide film (a gate oxide film) is formed on a p-type single crystal silicon substrate by the thermal oxidation method. Next, an about 100-nm-thick aluminum silicon mixing film including 60 atomic % of aluminum to the whole amount of aluminum and silicon was formed on a gate insulating film, which was a sensitive section, by using the magnetron sputtering method. A circular aluminum silicon-mixing target with the diameter of 4 inches (101.6 mm) was used as a target. What aluminum powder and silicon powder were sintered at a ratio of 60 atomic %:40 atomic % was used as the aluminum silicon mixing target. Sputter conditions were set at an Ar flow rate of 30 sccm, discharge pressure of 0.15 Pa, and supplied power of 100 W by using RF power. In addition, substrate temperature was set at 100° C.

In addition, the aluminum silicon mixing film was observed with the FE-SEM. In regard to a shape of a surface observed from an obliquely upper direction of the substrate, as shown in FIG. 8A, the circular aluminum pillar-shaped structures surrounded by the silicon domain were arranged two-dimensionally. The average pore diameter of an aluminum pillar-shaped structure portion was 10 nm, and its mean density was $1.5 \times 10^{11}$ pores/$cm^2$ or more. In addition, when a cross section was observed with the FE-SEM, each aluminum pillar-shaped structure was mutually independent.

Pores were formed by dipping the aluminum silicon mixing film produced in this way in a 98% of concentrated sulfuric acid solution for 24 hours to selectively etch only the aluminum pillar-shaped structure portions. As a result, the porous body which was composed of a member whose main component except oxygen was silicon was produced. In addition, silicon on the surface of the porous body was oxidized.

Next, the aluminum silicon mixing film (a porous body which was composed of the member whose main component except oxygen was silicon) having etched with the 98% of concentrated sulfuric acid was observed with the FE-SEM. In regard to a shape of a surface observed from an obliquely upper direction of the substrate, as shown in FIG. 8B, the pores surrounded by the silicon member were arranged two-dimensionally. The average pore diameter of pores was 10 nm, and mean density was $1.5 \times 10^{11}$ pores/$cm^2$ or more.

Next, the porous film produced in this way was annealed at 500° C. in an oxygen atmosphere. As a result, silicon in the porous film was oxidized and a porous film which is composed of a silicon oxide was formed on a silicon oxide (FIG. 7D). Next, the porous film and silicon oxide in an unnecessary portion are removed by photolithography, and dry etching or wet etching (FIG. 7E). Furthermore, a source region 128 and a drain region 129 are formed by using photolithography and ion implanter (FIG. 7F). The sensor in which the porous film which is composed of a silicon oxide is formed on the gate insulating film (a silicon oxide) as shown in FIG. 7F is formed through such processes.

In addition, the sensor used in this example is used under the environment where it is dipped in an aqueous solution. Accordingly, in order to perform insulation between the gate section and source region of the field-effect transistor for sensors, and between the gate section and drain region, it is preferable to form an insulating film and a passivation film on them (not shown).

Next, the detected material bonded with specific chemical substances is introduced in the pores in the porous film. Here, the case where biotin is used as the detected material will be simply explained. First, the porous film is processed by a silane-coupling agent. Next, a biotin is bonded inside the porous film by using biotin long arm. As a result, the sensor as shown in FIG. 4 is completed. In addition, when an amount of avidin, which is a biomaterial, in the sensor produced in this way was changed, its presence and a change of its amount could be read by the field-effect transistor.

According to the biosensor formed in this way, since it has the pore density of $1.5 \times 10^{11}$ pores/cm$^2$ or more, it is possible to arrange the detected material (here, biotin) in high density. As a result, it becomes possible to increase the measuring sensitivity remarkably. In addition, since it becomes possible to perform quick adhesion and detachment of chemical species, which are the detection material, because pores are almost perpendicular to the substrate and the pore diameter is almost constant, it becomes possible to produce the sensor which is excellent in the response. In addition, since the detected material is arranged inside the pores, it is possible to decrease measurement errors by the bonding of the detected material with other impurity larger than the pores.

In addition, in this example, although examples of avidin and biotin were shown as selective reactions of biomaterials, it is not limited to this but various selective reactions such as alternative reactions of streptavidin, biotin, and the like can be used.

EXAMPLE 3

This example shows the case that a sensor having a porous film, having pores which are perpendicular to a substrate and have cylindrical shapes, on a sensitive section (a gate insulating film) of a field-effect transistor is used as a pH sensor measuring pH of an acid and alkali solutions. Here, although the case that a material which constitutes the porous film is silicon except oxygen is shown, it is possible to adapt almost similar sensor structure, production method, and effects also in the case of germanium or a composite of silicon and germanium.

First, as shown in FIG. 6A, a 50-nm-thick silicon oxide film (a gate oxide film) is formed on a p-type single crystal silicon substrate by the thermal oxidation method. Next, on the silicon oxide film, an about 200-nm-thick aluminum silicon mixing film including 50 atomic % of aluminum to the whole amount of aluminum and silicon was formed on the silicon oxide, which is a gate insulating film, by using the magnetron sputtering method as shown in FIG. 6B. A circular aluminum silicon-mixing target with the diameter of 4 inches (101.6 mm) was used as a target. What aluminum powder and silicon powder were sintered at a ratio of 50 atomic %:50 atomic % was used as the aluminum silicon mixing target. Sputter conditions were set at an Ar flow rate of 30 sccm, discharge pressure of 0.15 Pa, and supplied power of 100 W by using RF power. In addition, substrate temperature was set at 100° C.

In addition, the aluminum silicon mixing film was observed with an FE-SEM. In regard to a shape of a surface observed from an obliquely upper direction of the substrate, as shown in FIG. 8A, the circular aluminum pillar-shaped structures surrounded by the silicon domain were arranged two-dimensionally. The average pore diameter of an aluminum pillar-shaped structure portion was 4 nm, and its mean density was $1.5 \times 10^{11}$ pores/cm$^2$ or more. In addition, when a cross section was observed with the FE-SEM, each aluminum pillar-shaped structure was mutually independent.

Pores were formed by dipping the aluminum silicon mixing film produced in this way in a 98% of concentrated sulfuric acid solution for 24 hours as shown in FIG. 6C to selectively etch only the aluminum pillar-shaped structure portions. As a result, the porous film which was composed of a member whose main component except oxygen was silicon was produced. In addition, silicon on the surface of the porous film was oxidized.

Next, the aluminum silicon mixing film (porous film which was composed of the member whose main component except oxygen was silicon) having etched with the 98% of concentrated sulfuric acid was observed with the FE-SEM. In regard to a shape of a surface observed from an obliquely upper direction of the substrate, as shown in FIG. 8B, the pores surrounded by the silicon member were arranged two-dimensionally. The pore diameter of pores was 4 nm, and mean pore density was $1.5 \times 10^{11}$ pores/cm$^2$ or more.

Next, the porous film produced in this way was annealed at 800° C. in a hydrogen atmosphere. As a result, silicon in the porous film was crystallized and a porous film which is composed of p-type polycrystalline silicon was formed on a silicon oxide (FIG. 7D). Next, the porous film and silicon oxide in unnecessary portions are removed by photolithography, and dry etching or wet etching (FIG. 7E). Furthermore, a source region and a drain region are formed by using photolithography and ion implanter (FIG. 7F). The sensor (pH sensor) which has the porous body film composed of polycrystalline silicon as shown in FIG. 7F is formed through such processes.

Next, the pore surfaces in the porous film were modified with triamino propylethoxysilane (3-APTES). As a result, the sensor as shown in FIG. 7F was completed.

In addition, when the sensor produced in this way was dipped in the solution whose pH was changed, it was possible to read the change by the field-effect transistor.

According to the pH sensor formed in this way, since the pore diameter is 4 nm and mean pore density is also $1.5 \times 10^{11}$ pores/cm$^2$ or more, it becomes possible to increase a specific surface area of the porous film remarkably, and hence, to increase the sensitivity remarkably. In addition, since it becomes possible to perform quick adhesion and detachment of chemical species because pores are almost perpendicular to the substrate and the pore diameter is almost constant, it becomes possible to produce the sensor which is excellent in the response.

This application claims priority from Japanese Patent Application No. 2003-291523 filed Aug. 11, 2003, which is hereby incorporated by reference herein.

The invention claimed is:

1. A method for producing a sensor that includes a field-effect transistor, the method comprising steps of:
   preparing a substrate that includes a gate insulating film;
   forming, by a sputtering method, a structure that includes a plurality of metallic pillar-shaped members disposed perpendicularly to the gate insulating film, and a structural member enclosing the plurality of metallic pillar-shaped members, the structural member including semiconductor material;
   removing the plurality of metallic pillar-shaped members to form a plurality of pillar-shaped pores in the structural member;
   annealing a porous film made of the structural member in which the plurality of pillar-shaped pores are formed; and
   utilizing the porous film as part of a sensitive section of the field-effect transistor.

* * * * *